(12) United States Patent
Reay-Young

(10) Patent No.: US 7,901,404 B2
(45) Date of Patent: Mar. 8, 2011

(54) BONE HARVESTING DEVICE AND METHOD

(75) Inventor: Clive Reay-Young, Harrogate (GB)

(73) Assignee: ArthroCare Corporation, Austin, TX (US)

( * ) Notice: Subject to any disclaimer, the term of this patent is extended or adjusted under 35 U.S.C. 154(b) by 1315 days.

(21) Appl. No.: 11/039,575

(22) Filed: Jan. 18, 2005

(65) Prior Publication Data

US 2005/0192582 A1    Sep. 1, 2005

Related U.S. Application Data

(60) Provisional application No. 60/537,078, filed on Jan. 16, 2004.

(51) Int. Cl.
*A61B 17/32* (2006.01)
(52) U.S. Cl. ........................................................ 606/79
(58) Field of Classification Search .................. 606/79, 606/84, 87, 88, 102; 144/114.1, 115; D8/47; 30/167.2
See application file for complete search history.

(56) References Cited

U.S. PATENT DOCUMENTS

| | | | |
|---|---|---|---|
| 1,727,590 A | | 9/1929 | Thomas |
| 2,778,357 A | | 1/1957 | Leibinger et al. |
| 2,848,020 A | * | 8/1958 | Zemrowski ............... 142/56 |
| 3,896,500 A | | 7/1975 | Rambert et al. |
| 3,905,356 A | | 9/1975 | Fletcher et al. |
| 3,973,277 A | | 8/1976 | Semple et al. |
| 3,974,621 A | | 8/1976 | Stang |
| 4,126,165 A | * | 11/1978 | Guignard et al. ........... 142/56 |
| 4,149,277 A | | 4/1979 | Bokros |
| 4,187,558 A | | 2/1980 | Dahlen et al. |
| 4,204,544 A | | 5/1980 | Feldstein et al. |
| 4,275,717 A | | 6/1981 | Bolesky |
| 4,309,778 A | * | 1/1982 | Buechel et al. ............ 623/20.29 |
| 4,335,715 A | | 6/1982 | Kirkley |
| 4,347,024 A | | 8/1982 | Coldren |
| 4,406,281 A | | 9/1983 | Hubbard et al. |
| 4,530,357 A | | 7/1985 | Pawloski et al. |
| 4,573,448 A | | 3/1986 | Kambin |
| 4,583,554 A | | 4/1986 | Mittelman et al. |
| 4,600,005 A | * | 7/1986 | Hendel ......................... 606/84 |
| 4,600,007 A | | 7/1986 | Lahodny et al. |
| 4,708,132 A | | 11/1987 | Silvestrini |
| 4,712,542 A | | 12/1987 | Daniel et al. |
| 4,759,350 A | * | 7/1988 | Dunn et al. ................... 606/82 |
| 4,776,851 A | | 10/1988 | Bruchman et al. |

(Continued)

FOREIGN PATENT DOCUMENTS

CH      681607      4/1991

(Continued)

OTHER PUBLICATIONS

PCT Notification of the International Search Report and Written Opnion for PCT/US06/19100, 7 pgs, Mailed Sep. 27, 2007.

(Continued)

*Primary Examiner* — Eduardo C Robert
*Assistant Examiner* — David Comstock
(74) *Attorney, Agent, or Firm* — Matthew Scheele; Brian Szymczak

(57) ABSTRACT

A surgical device and method are disclosed for harvesting bone portions. The device has a guide which facilitates control of at least one dimension of the harvested portion. Embodiments of the invention are particularly, but not exclusively, suited to harvesting bone portions for graft surgery, particularly patella tendon grafts.

30 Claims, 3 Drawing Sheets

U.S. PATENT DOCUMENTS

| | | | |
|---|---|---|---|
| 4,820,279 A | 4/1989 | Dedo | |
| 4,821,419 A * | 4/1989 | Lee | 30/493 |
| 4,969,471 A | 11/1990 | Daniel et al. | |
| 4,997,433 A | 3/1991 | Goble et al. | |
| 5,037,422 A | 8/1991 | Hayhurst et al. | |
| 5,037,426 A | 8/1991 | Goble et al. | |
| 5,139,520 A | 8/1992 | Rosenberg | |
| 5,147,361 A | 9/1992 | Ojima et al. | |
| D330,591 S | 10/1992 | Rosenberg et al. | |
| 5,152,790 A | 10/1992 | Rosenberg et al. | |
| 5,170,800 A | 12/1992 | Smith et al. | |
| 5,176,682 A | 1/1993 | Chow | |
| 5,176,699 A | 1/1993 | Markham | |
| 5,192,321 A * | 3/1993 | Strokon | 606/96 |
| 5,228,448 A | 7/1993 | Byrd | |
| 5,251,646 A | 10/1993 | Bowen | |
| 5,254,129 A | 10/1993 | Alexander | |
| 5,258,003 A | 11/1993 | Ciaglia et al. | |
| 5,266,075 A | 11/1993 | Clark et al. | |
| 5,303,472 A | 4/1994 | Mbanugo | |
| 5,306,301 A | 4/1994 | Graf et al. | |
| 5,314,429 A | 5/1994 | Goble et al. | |
| 5,324,308 A | 6/1994 | Pierce | |
| 5,330,468 A | 7/1994 | Burkhart | |
| 5,350,380 A | 9/1994 | Goble et al. | |
| 5,350,383 A | 9/1994 | Schmieding et al. | |
| 5,364,400 A | 11/1994 | Rego, Jr. et al. | |
| 5,383,471 A | 1/1995 | Funnell | |
| 5,391,169 A * | 2/1995 | McGuire | 606/79 |
| 5,393,302 A | 2/1995 | Clark et al. | |
| RE34,871 E | 3/1995 | McGuire et al. | |
| 5,395,375 A | 3/1995 | Turkel et al. | |
| 5,405,359 A | 4/1995 | Pierce | |
| 5,408,359 A | 4/1995 | Ferrett et al. | |
| 5,423,860 A | 6/1995 | Lizardi et al. | |
| 5,472,452 A | 12/1995 | Trott | |
| 5,475,553 A | 12/1995 | Saliba | |
| 5,489,292 A | 2/1996 | Tovey et al. | |
| 5,529,424 A | 6/1996 | Neubert et al. | |
| 5,556,411 A | 9/1996 | Taoda et al. | |
| 5,562,664 A | 10/1996 | Durlacher et al. | |
| 5,591,190 A | 1/1997 | Yoon | |
| 5,601,562 A | 2/1997 | Wolf et al. | |
| 5,609,634 A | 3/1997 | Voydeville | |
| 5,618,314 A | 4/1997 | Harwin et al. | |
| 5,620,001 A | 4/1997 | Byrd et al. | |
| 5,626,609 A | 5/1997 | Zvenyatsky et al. | |
| 5,632,748 A | 5/1997 | Beck et al. | |
| 5,643,266 A | 7/1997 | Li | |
| 5,643,273 A | 7/1997 | Clark | |
| 5,645,588 A | 7/1997 | Graf et al. | |
| 5,647,874 A | 7/1997 | Hayhurst | |
| 5,651,368 A | 7/1997 | Napolitano et al. | |
| 5,674,224 A | 10/1997 | Howell et al. | |
| 5,683,359 A | 11/1997 | Farkas et al. | |
| 5,683,406 A * | 11/1997 | Altobelli et al. | 606/170 |
| 5,683,471 A | 11/1997 | Incavo et al. | |
| 5,707,395 A | 1/1998 | Li | |
| 5,725,541 A | 3/1998 | Anspach et al. | |
| 5,735,867 A | 4/1998 | Golser et al. | |
| 5,769,894 A | 6/1998 | Ferragamo | |
| 5,782,749 A | 7/1998 | Riza | |
| 5,788,701 A | 8/1998 | McCue | |
| 5,797,963 A | 8/1998 | McDevitt | |
| 5,813,808 A | 9/1998 | Wu | |
| 5,840,078 A | 11/1998 | Yerys | |
| 5,891,150 A | 4/1999 | Chan | |
| 5,891,168 A | 4/1999 | Thal | |
| 5,895,425 A | 4/1999 | Grafton et al. | |
| 5,911,695 A | 6/1999 | Watkins et al. | |
| 5,913,860 A | 6/1999 | Scholl | |
| 5,935,129 A | 8/1999 | McDevitt et al. | |
| 5,984,966 A | 11/1999 | Kiema et al. | |
| 5,989,253 A | 11/1999 | Bigliardi | |
| 6,015,412 A | 1/2000 | Mifsud | |
| 6,068,648 A | 5/2000 | Cole et al. | |
| D426,305 S | 6/2000 | Hein | |
| 6,080,154 A | 6/2000 | Reay-Young et al. | |
| 6,086,591 A | 7/2000 | Bojarski | |
| 6,099,568 A | 8/2000 | Simonian et al. | |
| 6,110,207 A | 8/2000 | Eichhorn et al. | |
| 6,117,161 A | 9/2000 | Li et al. | |
| 6,132,433 A | 10/2000 | Whelan | |
| 6,146,406 A | 11/2000 | Shluzas et al. | |
| 6,146,407 A | 11/2000 | Krebs | |
| 6,152,928 A | 11/2000 | Wenstrom | |
| 6,156,039 A | 12/2000 | Thal | |
| 6,187,011 B1 | 2/2001 | Torrie | |
| 6,214,007 B1 | 4/2001 | Anderson | |
| 6,221,107 B1 | 4/2001 | Steiner et al. | |
| 6,224,603 B1 * | 5/2001 | Marino | 606/79 |
| 6,254,606 B1 | 7/2001 | Carney et al. | |
| 6,306,138 B1 | 10/2001 | Clark et al. | |
| 6,319,270 B1 | 11/2001 | Grafton et al. | |
| 6,328,758 B1 | 12/2001 | Tornier et al. | |
| 6,355,053 B1 | 3/2002 | Li | |
| 6,355,066 B1 | 3/2002 | Kim | |
| 6,371,124 B1 | 4/2002 | Whelan | |
| 6,379,361 B1 | 4/2002 | Beck, Jr. et al. | |
| 6,440,134 B1 | 8/2002 | Zaccherotti et al. | |
| 6,478,753 B2 | 11/2002 | Reay-Young | |
| 6,491,714 B1 | 12/2002 | Bennett | |
| 6,499,486 B1 | 12/2002 | Chervitz et al. | |
| 6,517,578 B2 | 2/2003 | Hein | |
| 6,527,795 B1 | 3/2003 | Lizardi | |
| 6,533,816 B2 | 3/2003 | Sklar | |
| 6,544,273 B1 | 4/2003 | Harari et al. | |
| 6,547,800 B2 | 4/2003 | Foerster et al. | |
| 6,551,343 B1 | 4/2003 | Tormala et al. | |
| 6,562,071 B2 | 5/2003 | Jarvinen | |
| 6,610,064 B1 | 8/2003 | Goble et al. | |
| 6,610,080 B2 | 8/2003 | Morgan | |
| 6,623,524 B2 | 9/2003 | Schmieding | |
| 6,635,074 B2 | 10/2003 | Bartlett | |
| 6,652,533 B2 | 11/2003 | O'Neil | |
| 6,652,560 B1 | 11/2003 | Gerke et al. | |
| 6,736,847 B2 | 5/2004 | Seyr et al. | |
| 6,780,188 B2 | 8/2004 | Clark et al. | |
| 6,802,862 B1 | 10/2004 | Roger et al. | |
| 6,808,528 B2 | 10/2004 | Justin | |
| 6,878,166 B2 | 4/2005 | Clark et al. | |
| 6,905,513 B1 | 6/2005 | Metzger | |
| 6,991,631 B2 | 1/2006 | Woloszko et al. | |
| 6,994,725 B1 | 2/2006 | Goble | |
| 7,175,632 B2 | 2/2007 | Singhatat et al. | |
| 7,226,469 B2 | 6/2007 | Benavitz et al. | |
| D547,451 S | 7/2007 | Asfora | |
| 2004/0193167 A1 | 9/2004 | Tucciarone et al. | |
| 2005/0192582 A1 | 9/2005 | Reay-Young | |
| 2005/0222619 A1 | 10/2005 | Dreyfuss et al. | |
| 2006/0178673 A1 | 8/2006 | Curran | |
| 2006/0235516 A1 | 10/2006 | Cavazzoni | |
| 2006/0253119 A1 | 11/2006 | Berberich et al. | |
| 2006/0271059 A1 | 11/2006 | Reay-Young et al. | |
| 2006/0276841 A1 | 12/2006 | Barbieri et al. | |
| 2007/0021751 A1 | 1/2007 | Reay-Young et al. | |
| 2007/0213730 A1 | 9/2007 | Martinek et al. | |
| 2007/0260249 A1 | 11/2007 | Boyajian et al. | |

FOREIGN PATENT DOCUMENTS

| | | |
|---|---|---|
| DE | 9002844 | 1/1991 |
| DE | 29607352 | 9/1996 |
| EP | 238223 | 9/1987 |
| EP | 279129 | 8/1988 |
| EP | 317406 | 5/1989 |
| EP | 379789 | 11/1989 |
| EP | 346469 | 12/1989 |
| EP | 574707 | 12/1993 |
| EP | 619982 | 3/1994 |
| EP | 0 674 880 | 3/1995 |
| EP | 706780 | 4/1996 |
| EP | 0865774 | 9/1998 |
| EP | 1066805 | 6/2000 |
| EP | 1180351 | 2/2002 |
| FR | 2395012 | 1/1979 |
| FR | 2590792 | 6/1987 |
| FR | 2683715 | 5/1993 |

| | | |
|---|---|---|
| FR | 2725615 | 4/1996 |
| FR | 2732211 | 4/1996 |
| GB | 2288739 | 11/1995 |
| GB | 2337463 | 11/1999 |
| SU | 1521465 | 11/1989 |
| WO | 93/25148 | 12/1993 |
| WO | 95/11631 | 5/1995 |
| WO | 96/03926 | 2/1996 |
| WO | 96/29029 | 9/1996 |
| WO | 96/39934 | 12/1996 |
| WO | 97/19634 | 6/1997 |
| WO | 97/20522 | 6/1997 |
| WO | 98/12991 | 4/1998 |
| WO | 98/12992 | 4/1998 |
| WO | 98/22048 | 5/1998 |
| WO | 98/38937 | 9/1998 |
| WO | 99/52472 | 10/1999 |
| WO | 99/59488 | 11/1999 |
| WO | 03/088874 | 10/2003 |

OTHER PUBLICATIONS

PCT Notification of the International Search Report and Written Opninon for PCT/US05/17382, 11 pgs, Mailed Oct. 23, 2007.

Smith & Nephew, "Arthroscopic Repair of a Bankart Lesion Using TAG Suture Anchors," 12 pgs, May 1996.

F.H. Fuh, et al., Anatomic ACL Double-Bundle Reconstruction, Orthopedic Technology Review vol. 7 No. 4, 6 pgs, 2005.

ArthroCare SportsMedicine Product Catalogue, 3.1 Knee (p. 44 p. 52), 4 pgs, Jul. 2005.

PCT Notification of the International Search Report and Written Opninon for PCT/US05/01629, 6 pgs, Mailed Apr. 22, 2008.

European Search Report for EP 97122626 2 pgs, Apr. 21, 1998.

* cited by examiner

BONE HARVESTING DEVICE AND METHOD

CROSS-REFERENCE TO RELATED APPLICATIONS

This application claims the benefit under 35 U.S.C. § 119 (e) of U.S. Provisional Patent Application No. 60/537,078, filed Jan. 16, 2004.

BACKGROUND OF THE INVENTION

The present invention relates to bone harvesting device and method.

FIELD OF THE INVENTION

The Invention relates particularly but not exclusively to devices and methods for harvesting bone samples. Embodiments are particularly but not exclusively optimised for use in ligament graft surgery.

DESCRIPTION OF THE RELATED ART

A problem faced in bone block harvesting, particularly in graft surgery, is harvesting the bone blocks accurately and quickly, while minimising damage to the donor site. It is desirable to reduce the operative time as much as possible, since a shorter operation generally results in faster recovery for the patient and a reduced risk of complications. In addition, the bone blocks harvested should have a precise desired size and shape to allow them to be positioned in their intended destination, which may be a bone tunnel for example, and to provide a good fit with the destination site to facilitate fusion of the bone block with the surrounding bone.

Bone block harvesting is usually carried out using a combination of osteotomes (bone chisels) and powered micro saw blades. One prior art harvesting technique involves simply using an end cutting oscillating saw to cut a bone block, whose dimensions are determined either by judgement or using a ruler, and subsequently freeing the base of the block using an osteotome. This technique may be problematic, for example in harvesting bone blocks associated with the patellar tendon, in which procedure the nature of the patella makes controlling the depth to which the patella bone is cut very difficult. The depth of the bone block is especially hard to control. As a result irregular bone blocks are produced that have to be subsequently cut to size and shaped, which is time consuming and wastes bone stock.

In prior art techniques using osteotomes and bone saws, both the quality of bone block harvested and the amount of damage to the donor site are substantially dependent on the skill of the surgeon. It would be desirable to be able to produce accurate bone blocks in a more reliable way which is less demanding for the surgeon. In addition, in prior art methods using a powered bone saw there is a risk of thermal damage to the surrounding tissue at the donor site caused by the action of the saw.

In another example of a prior art bone harvesting method, a template is pinned onto the surface of the bone from which the bone block is to be taken, and a saw is used to cut through the bone along the edges of the template. In this technique the dimensions of the bone block are controlled, but it has the disadvantage of added complexity. Extra surgical steps are required to attach and subsequently remove the template, and the process of cutting to the template is also time consuming, so the duration of the surgery is increased and the demands on the surgeon are greater.

SUMMARY OF THE INVENTION

In a first aspect of the invention there is provided a bone block harvester for harvesting a bone block, comprising a body having a proximal end and a distal end; a cutter disposed at the distal end of the harvester; and a cutting guide coupled to the cutter and having a tissue contact surface spaced from the cutter, arranged to guide the motion of the cutter to control a dimension of the bone block.

Thus, in contrast to conventional bone cutting devices which generally aim to provide a surgeon with greater control over the device, the invention aims to restrict movement, in at least one dimension, by bearing on a tissue surface. As used in this context, the term "tissue" may include bone or soft tissue, typically bone or tendon. The dimension, most advantageously depth, may be tightly controlled, the guide preferably rigidly determining a maximum value. However, the guide may have some degree of resilience or flexibility to allow the surgeon to make fine adjustments to the controlled dimension based on tactile feedback from the guide.

Preferably, the bone block harvester is arranged to determine a dimension of the bone block in a direction substantially perpendicular to the direction of motion of the cutter. This may allow the surgeon one or two other degrees of freedom to control depth or width with a particular harvester being optimised for a particular depth.

In a preferred arrangement, the cutting guide comprises a guiding element having a controlled distance of separation from the cutting means. Preferably, the guiding element is substantially rigidly attached to the body of the harvester.

In a convenient arrangement, the guiding element is coupled by an elongate arm to the cutter. Advantageously, the cutter is elongate and the elongate arm extends substantially parallel to and spaced from the elongate cutter. This arrangement is both readily manufactured and easily usable. Preferably the spacing of the arm and cutter determines one dimension of the bone block.

Although the surgeon may have substantial freedom of movement in dimensions other than the controlled dimension, advantageously a stop determines a maximum value for a further dimension of the bone block. Projections perpendicular to the direction of elongation of the cutter wherein the projections may be arranged to limit the depth of penetration of the cutter into a bone.

Conveniently the cutter comprises a blade having a width and the blade width corresponds to a width of the bone block.

The cutter may comprise a generally flat blade having a width and the elongate arm is preferably attached to the blade substantially at one side. The attachment may form a guide or cutter for a side of the bone block or, more typically, may be set back so as not to impede cutting.

The guiding element preferably extends in the direction of the width of the blade further than the width of the elongate arm; this enables a more reliable guide without requiring an unwieldy attachment arm, and may enable the guiding element to be hooked onto a tendon. Preferably the guiding element has substantially the same width as the cutter blade.

The cutting guide is preferably substantially blunt and/or may have rounded contact edges. In contrast, the cutter preferably has a sharpened flat distal edge (although it may in some cases have a sharpened point or curved edge). This facilitates harvesting a generally rectangular section (e.g. cuboid or trapezoid) portion of bone. The cutter may be elongate and the side edges of the cutter are preferably less sharp than the distal edge, optionally substantially blunt.

A handle may be provided at the proximal end of the body, although an attachment for another tool (e.g. robotic tool) may be provided alternatively.

Preferably the body is elongate and comprises a substantially linear proximal portion and a curved distal portion; this facilitates manipulation. The curved distal portion of the harvester may allow the handle of the harvester to be held at an angle to the direction of cutting, which is highly advantageous where the region proximal the cutting edge is obstructed.

In a preferred embodiment the bone block harvester is dimensioned and arranged to harvest a bone block for use in anterior cruciate ligament reconstruction surgery, wherein the bone block comprises a block of bone from the patella or superior tibia of a patient, the cutting guide is arranged to abut the top surface of the patella tendon in a first position where the distal edge of the cutter is at the surface of the patella, wherein the cutting guide is arranged to abut the top of the patella or superior tibia in a second position where the cutting means is inserted into the bone, and wherein the cutting guide is arranged to move from the patella tendon to the bone as the harvester is moved from the first position to the second position.

The cutting guide may be arranged to engage either soft tissue or bone. Preferably the cutting guide is arranged to contact soft tissue during an initial stage of cutting and a bone surface at a later stage of cutting. Preferably the cutting guide is shaped to hook over a tendon to guide an initial cutting stage. Advantageously the cutting guide is further arranged to ride over the surface of a bone to guide a later cutting stage.

In a second aspect, the invention provides a method of harvesting a bone block comprising:
providing a bone harvester having a cutter and a cutting guide; positioning the bone harvester in a first position in which the cutting guide abuts a tissue surface; cutting bone with the cutter while moving the bone harvester to a second position, the cutting guide controlling motion of the cutter in at least one dimension.

In a third aspect, the invention provides a method of harvesting a graft including a portion of patella tendon and bone, the method comprising: providing a bone harvester having a cutter and a cutting guide; positioning the bone harvester so that the cutting guide contacts the patella tendon and the cutter contacts the patella; moving the bone harvester to cut into the patella with the cutting guide guiding the motion of the cutter.

In a fourth aspect, the invention provides a method of harvesting a portion of bone to provide a graft, the method comprising cutting a portion of bone with a cutter wherein the depth of the portion is controlled by a cutting guide coupled to the cutter.

In a fifth aspect, the invention provides a kit comprising a bone block harvester having a cutter and a cutting guide and instructions for harvesting a portion of bone comprising cutting the portion of bone with the cutter while the cutting guide contacts tissue to control a dimension of the portion of bone.

The harvester according to the invention may be applicable to a range of surgical procedures, but it is particularly advantageous in patellar tendon graft harvesting, where controlling the depth of a patella bone block is a problem. As well as graft harvesting, the apparatus and methods may be used for obtaining tissue samples from living or dead subjects, in human or veterinary procedures. Each feature disclosed herein may be independently provided unless otherwise stated and preferred features of each aspect may be applied in alternative combinations and to other aspects.

BRIEF DESCRIPTION OF THE DRAWINGS

Embodiments of the invention will now be described with reference to the accompanying drawings in which.

DETAILED DESCRIPTION OF PREFERRED EMBODIMENTS

In a preferred embodiment, described below by way of example only, there is provided a bone block harvester for use in Anterior Cruciate Ligament graft surgery using a Patellar Tendon graft.

Anterior Cruciate Ligament (ACL) reconstruction surgery involves replacing a torn ACL with a graft ligament that can be taken from the patient's own body (autologous) or made from synthetic material or from a cadaver (allograft). Of the total number of surgeries performed around 85% are performed using autologous grafts. Of this number approximately 65% are performed using a graft ligament taken from the central third of the Patellar Tendon, including bone from the superior tibia and the patella. These are referred to as Bone-Patellar Tendon-Bone (BPTB) grafts. There are several alternative grafts available for ACL reconstruction, including hamstring grafts and allografts, but the BPTB graft offers the advantage that the bone blocks heal into the surrounding bone of the patient after the attachment of the graft, providing fixation as strong as that of the original ACL.

Figure 1:
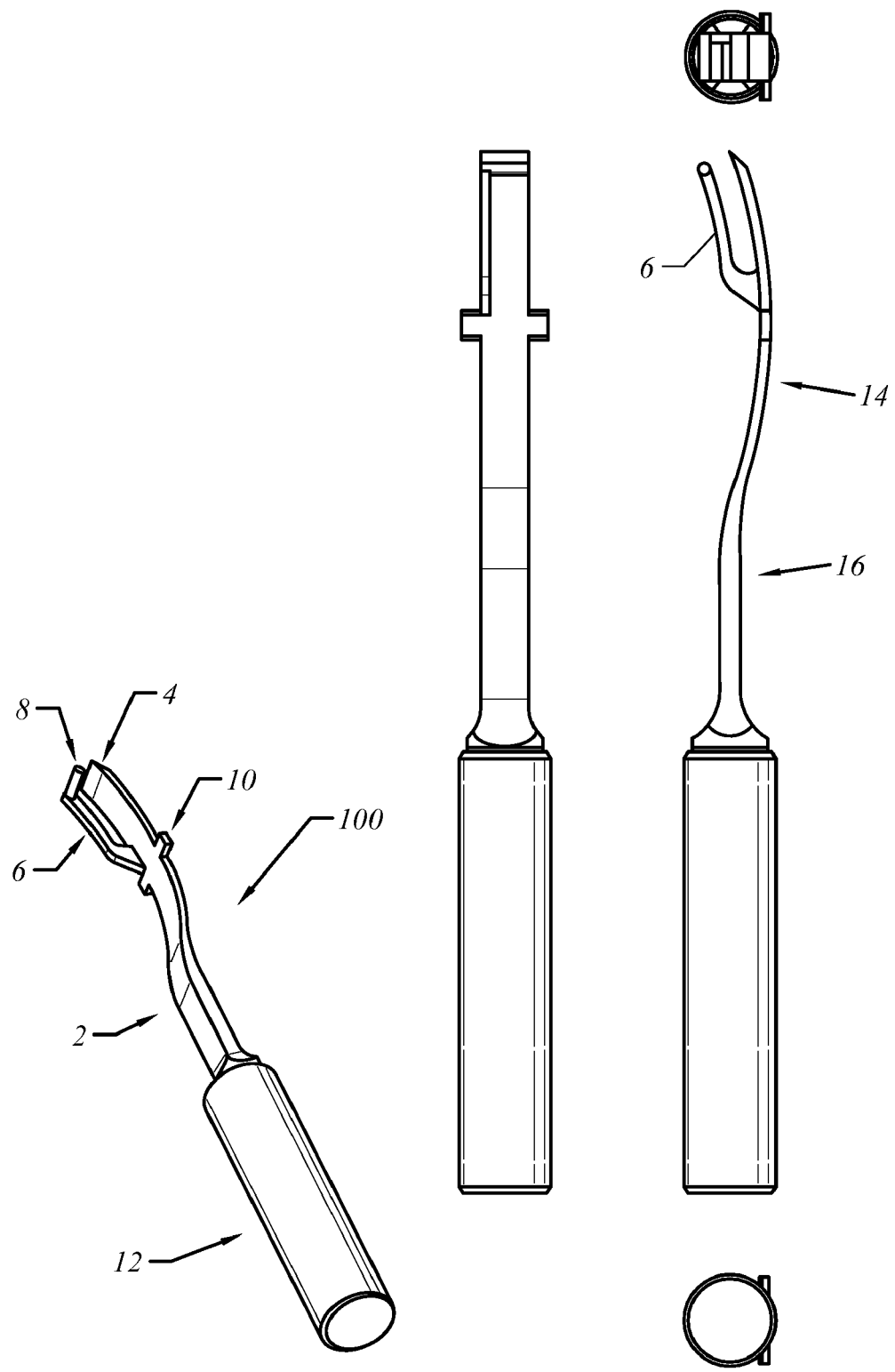
FIG. 1 shows projections of a bone block harvester according to one embodiment of the invention.

With reference to FIG. 1, the harvester 100 comprises a cylindrical handle 12 rigidly joined to an elongate body 2 extending substantially along the axis of the handle 12. The body 2, as shown in this embodiment, is a strip of rectangular cross section which is straight over a proximal portion 16, and curves vertically, i.e. in a plane parallel to the axis of the handle 12 and perpendicular to the largest side of the strip 2, over a distal portion 14. There are two projections 10 of the strip 2 laterally in the distal portion 14, near the lowest point of the curved section, which limit the length of the bone block harvested.

The tip of the body 2 comprises a chiseled cutting edge 4 for cutting into the bone to be harvested. A coupling bar 6 is mounted to the body 2, the bar 6 running approximately parallel to the body 2 at the distal end of the body 2 between the lateral projections 10 and the cutting edge 4. The bar 6 is disposed above the body 2 and to one side, and curves down to join the body at one of the lateral projections 10. At the tip of the coupling bar 6, above the cutting edge 4, a perpendicular guiding bar 8 is mounted extending across the width of the cutting edge 4. The guiding bar arrangement controls the depth of the bone block harvested.

Figure 2:
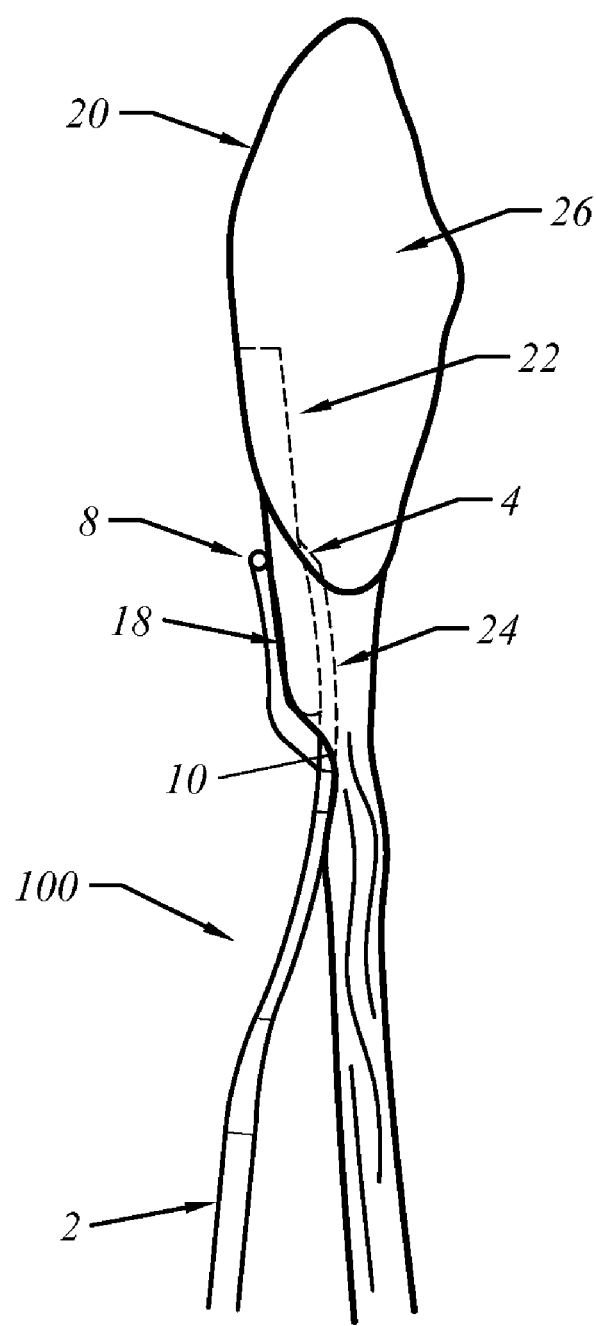
FIG. 2 shows a side view of an embodiment of the invention in use, with the cutting edge just engaging the bone surface.
Figure 3:
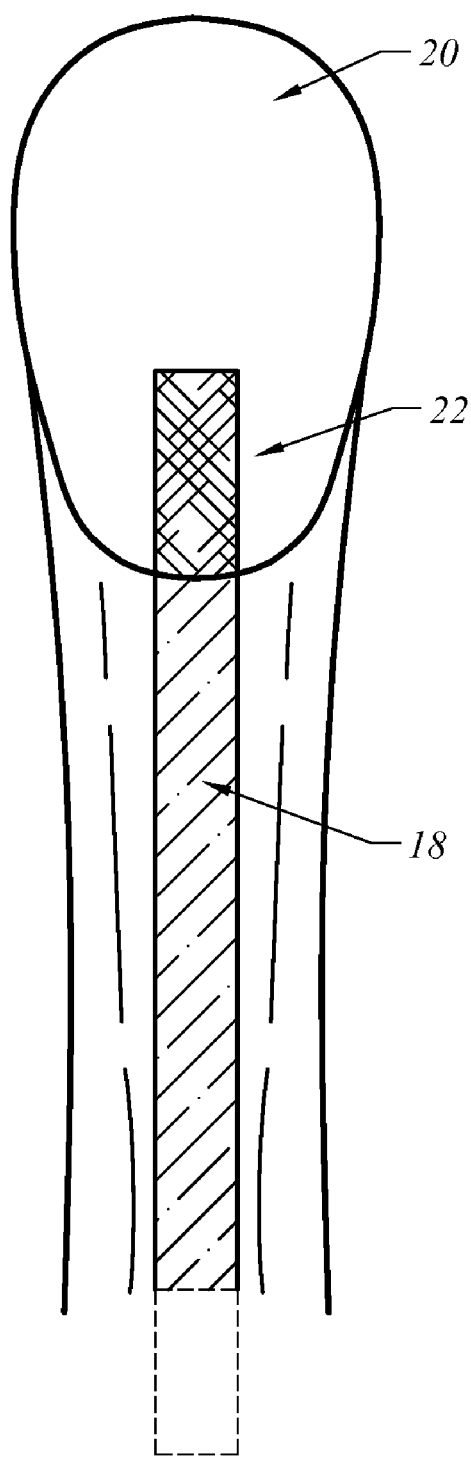
FIG. 3 is a schematic diagram of the patella, patella tendon and tibia, showing steps in a graft procedure in which an embodiment of the invention may be used.

A possible method for using the harvester will now be described with reference to FIG. 2. Prior to the harvester being used, the central third of the patellar tendon 24 is separated from the surrounding tendon. In the operation of the harvester 100, the guiding bar 8 is positioned to abut the upper surface 18 of the central third of the patellar tendon and the cutting edge 4 is disposed beneath the tendon 24. The surgeon operates the harvester using the handle 12, held at an angle to the patellar tendon 24. The surgeon applies sufficient force to the handle to slide the cutting edge 4 into the patella 26. As the cutting edge 4 of the harvester 100 is pushed into the patella 26, the guiding bar 8 rides over the upper surface of the tendon 18 and then the upper surface of the patella 20, ensuring that the cutting edge 4 follows a substantially horizontal path through the bone at a predetermined maximum depth defined by the vertical distance between the guiding bar 8 and the cutting edge 4. The length of the bone block 22 is limited by the lateral projections 10 disposed partway along the curved distal portion of the body 2, which abut the front surface of the patella 26 and prevent further intrusion of the cutting edge 4 into the bone when a predetermined maximum length of bone block 22 is reached.

When harvesting a bone block, by cutting as deep as the guiding bar will allow, and optionally cutting to the length allowed by the lateral projections, using an embodiment of the present invention the surgeon can easily ensure that an even, appropriately sized and shaped bone block is produced, while minimising the risk of damage to the donor site. The device can be made in as many different widths as a surgeon may require and can also be manufactured to allow the depth of the bone block to be controlled to the surgeon's requirements.

In an alternative embodiment, not shown, the size of the controlled dimension (depth) of the bone block may be adjustable, for example by having the arm position adjusted by a set screw. However, for ease of use and sterilization, preferably the depth is fixed for a given instrument. A set of instruments may be provided wherein the respective sizes of the controlled dimensions of the bone block are mutually different. For example, a set of standard increments may be provided, for example 3, 4, 5, 6,7,8 mm depths.

The harvester may be used for various applications and various sizes of bone blocks. Preferred bone block controlled dimensions, preferably depths, are at least 1 mm and preferably no more than 10 mm, more preferably 3-8 mm. The width of the harvested portion is preferably at least 3 mm wide and preferably no wider than 20 mm, more preferably 5 to 15 mm, most preferably 6-12 mm. The length of the harvested portion, which may be selected by the surgeon by adjusting the depth of penetration of the cutter is preferably no longer than 50 mm, preferably less than about 25 mm (1 inch). The length is preferably at least 3 mm, typically at least 5 or 10 mm. The dimensions may be independently chosen. However, the device is most suitable for harvesting a bone block having a depth in the range about 3 to 8 mm, a width in the range of about 6 to 12 mm and a length of about 5 to 25 mm.

The embodiment described above is not intended to be limiting and it will be appreciated that other embodiments are possible within the scope of the invention as defined by the following claims. Specifically, the bone block harvester may be used in several different surgical procedures and the application of the invention is not limited to any one type of surgery unless so limited by the attached claims.

The invention claimed is:

1. A bone block harvester for harvesting a bone block, comprising:
   a body having a proximal end and a distal end;
   a cutter disposed at the distal end of the harvester, the cutter having a width;
   a coupling bar having a proximal end and a distal tip, wherein the coupling bar proximal end is connected to the body distal end, and wherein the coupling bar extends distally; and
   wherein the coupling bar comprises a cutting guide bar, the cutting guide bar disposed at the distal tip of the coupling bar and extends perpendicularly to the coupling bar and substantially across the width of the cutter, the cutting guide bar having a tissue contact surface spaced above the cutter, arranged to guide the motion of the cutter to control a dimension of the bone block.

2. A bone block harvester according to claim 1 arranged to control a dimension of the bone block in a direction substantially perpendicular to the direction of motion of the cutter.

3. A bone block harvester according to claim 1, wherein the cutting guide bar is disposed at a controlled distance of separation from the cutter.

4. A bone block harvester according to claim 1, wherein the coupling bar is substantially rigidly attached to the body of the harvester.

5. A bone block harvester according to claim 1 wherein the cutter is elongate and wherein the coupling bar extends substantially parallel to and spaced from the elongate cutter.

6. A bone block harvester according to claim 1 wherein the spacing of the cutting guide bar and cutter determines one dimension of the bone block.

7. A bone block harvester according to claim 1 wherein a stop determines a maximum value for a further dimension of the bone block.

8. A bone block harvester according to claim 1 wherein the cutter comprises a blade having a width and wherein the blade width corresponds to a width of the bone block.

9. A bone block harvester according to claim 1 wherein the cutter comprises a generally flat blade having a width.

10. A bone block harvester according to claim 9 wherein the cutting guide bar extends in the direction of the width of the blade further than the width of the coupling bar.

11. A bone block harvester according to claim 10 wherein the cutting guide bar has substantially the same width as the cutter blade.

12. A bone block harvester according to claim 1 wherein the cutting guide bar is substantially blunt.

13. A bone block harvester according to claim 1 wherein the cutting guide bar has rounded contact edges.

14. A bone block harvester according to claim 1 wherein the cutter has a sharpened flat distal edge.

15. A bone block harvester according to claim 14 wherein the cutter is elongate and the side edges of the cutter are less sharp than the distal edge, optionally substantially blunt.

16. A bone block harvester according to claim 1, further comprising a handle at the proximal end of the body.

17. A bone block harvester according to claim 1, further comprising projections perpendicular to the direction of elongation of the cutter wherein the projections are disposed adjacent the coupling bar proximal end and are arranged to limit the depth of penetration of the cutter into a bone.

18. A bone block harvester according to claim 1, wherein the body is elongate and comprises a substantially linear proximal portion and a curved distal portion.

19. A bone block harvester according to claim 1 dimensioned and arranged to harvest a bone block for use in anterior cruciate ligament reconstruction surgery, wherein the bone block comprises a block of bone from the patella or superior tibia of a patient, the cutting guide bar is arranged to abut the top surface of the patella tendon in a first position where the distal edge of the cutter is at the surface of the patella, wherein the cutting guide bar is arranged to abut the top of the patella or superior tibia in a second position where the cutter is inserted into the bone, and wherein the cutting guide bar is arranged to move from the patella tendon to the bone as the harvester is moved from the first position to the second position.

20. A bone block harvester according to claim 1 wherein the cutting guide bar is arranged to engage either soft tissue or bone.

21. A bone block harvester according to claim 20 wherein the cutting guide bar is arranged to contact soft tissue during an initial stage of cutting and a bone surface at a later stage of cutting.

22. A bone block harvester according to claim 20 wherein the cutting guide bar is shaped to hook over a tendon to guide an initial cutting stage.

23. A bone block harvester according to claim 22 wherein the cutting guide bar is further arranged to ride over the surface of a bone to guide a later cutting stage.

24. A bone block harvester according to claim 1 wherein the size of the controlled dimension of the bone block is adjustable.

25. A bone block harvester according to claim 1 wherein the size of the controlled dimension of the bone block is substantially fixed.

26. A kit comprising a plurality of bone block harvesters according to claim 25, wherein the respective sizes of the controlled dimensions of the bone block are mutually different.

27. A bone block harvester according to claim 1 arranged to harvest a bone block having a depth in the range of about 3 to 8 mm, a width in the range of about 6 to 12 mm and a length of about 5 to 25 mm.

28. A method of harvesting a bone block comprising:
   positioning a bone harvester having a cutter and a cutting guide bar in a first position in which the cutting guide bar is disposed substantially across the width of the cutter and abuts a tissue surface at a location laterally spaced away from the cutter;
   cutting bone with the cutter while moving the bone harvester to a second position, the cutting guide bar controlling motion of the cutter in at least one dimension.

29. A method of harvesting a graft including a portion of patella tendon and bone, the method comprising:
   positioning a bone harvester having a cutter and a cutting guide bar so that the cutting guide bar contacts the patella tendon and the cutter contacts the patella, wherein the cutting guide bar is disposed substantially across the width of the cutter and is laterally spaced away from the cutter;
   moving the bone harvester to cut into the patella with the cutting guide bar guiding the motion of the cutter and riding over the surface of the tendon substantially above the cutter.

30. A method of harvesting a bone block comprising:
   positioning a bone harvester having a cutter, at least one lateral projection disposed partway along the bone harvester and a cutting guide having a cutting guide bar disposed at the distal tip of the cutting guide, in which the cutting guide bar abuts a tissue surface at a location laterally spaced above and across the width of the cutter;
   moving the harvester so as to simultaneously cut into the tissue with the cutter while the cutting guide bar simultaneously rides across the tissue surface directly above the cutter, the cutting guide controlling motion of the cutter in at least one dimension; and
   abutting the at least one lateral projection with the tissue surface to stop the harvester motion.

\* \* \* \* \*